US008173379B2

(12) United States Patent
Mallwitz et al.

(10) Patent No.: US 8,173,379 B2
(45) Date of Patent: May 8, 2012

(54) METHOD OF DETERMINING A CONCENTRATION OF ANALYTES OF INTEREST IN A SAMPLE

(75) Inventors: Frank Mallwitz, Berlin (DE); Ursula Dahmen-Levison, Berlin (DE); Derek Levison, Berlin (DE); Stuart Levison, Edgewater, NJ (US)

(73) Assignee: Aokin AG, Berlin (DE)

( * ) Notice: Subject to any disclaimer, the term of this patent is extended or adjusted under 35 U.S.C. 154(b) by 201 days.

(21) Appl. No.: 12/674,254

(22) PCT Filed: Jul. 15, 2008

(86) PCT No.: PCT/EP2008/059246
§ 371 (c)(1),
(2), (4) Date: Feb. 19, 2010

(87) PCT Pub. No.: WO2009/024413
PCT Pub. Date: Feb. 26, 2009

(65) Prior Publication Data
US 2011/0262936 A1    Oct. 27, 2011

(30) Foreign Application Priority Data

Aug. 23, 2007  (EP) .................................. 07114855
Oct. 11, 2007  (EP) .................................. 07118281

(51) Int. Cl.
*G01N 33/53*    (2006.01)

(52) U.S. Cl. ............ 435/7.21; 435/7.1; 436/1; 436/501; 436/518; 424/9.1; 424/520; 422/1; 422/50; 530/300; 530/350

(58) Field of Classification Search .................. None
See application file for complete search history.

(56) References Cited

U.S. PATENT DOCUMENTS
6,025,917 A    2/2000 Toyonaga et al.

FOREIGN PATENT DOCUMENTS
WO  WO 2004/068115 A  8/2004

OTHER PUBLICATIONS

Levison et al., Fluorescence Polarization Measurement of the Hormone-Binding Site Interaction; Endocrinology, 99(4) 1129-1143 (1976).

Dandliker et al., Equilibrium and Kinetic Inhibition Assays Based upon Fluorescence Polarization; Methods Enzymol, 74 Pt C:3-29 (1981).
Matveeva et al., Use of Stopped-flow Fluoroimmunoassay in Pesticide Determination; Analyst, 122, 863-866 (1997).
Eremin, S.A. et al. (1998) Kinetic Determination of 2,4-Dichlorophenoxyacetic Acid by Stopped-Flow Fluorescence Polarization Immunoassay, International Journal of Environmental Analalytical Chemistry, 71 (2): 137-146.
Gomez-Hens, A. et al. (May 2003) Stopped-flow Fluorescence Polarization Immunoassay, Current Topics in Medicinal Chemistry, 6 (3): 177-182.
Maragos, C.M. et al. (Mar. 26, 2002) Rapid Fluorescence Polarization Immunoassay for the Mycotoxin Deoxynivalenol in Wheat, Journal of Agricultural and Food Chemistry, 50 (7): 1827-1832.
Perez-Bendito, D. et al. (Aug. 1994) Direct Stopped-Flow Fluorescence Polarization Immunoassay of Abused Drugs and Their Metabolites in Urine, Clinical Chemistry, 40 (8): 1489-1493.
Perez-Bendito, D. et al. (1996) Advances in drug analysis by kinetic methods, Journal of Pharmaceutical and Biomedical Analysis, 14 (8/10): 917-930.
Sanchez-Martinez, M.L. et al. (Nov. 27, 2006) Long-wavelength fluorescence polarization immunoassay for surfactant determination, Talanta, Elsevier, 72: 243-248.
Maragos et al., J. Agricultural and Food Chemistry, 50, 1827-1832 (published online Feb. 26, 2002).
Levison et al., Fluorescence Polarization Measurement of the Hormone-Binding Site Interaction, Endocrinology, 99(4):1129-1143 (Oct. 1976).
Dandliker et al., Equilibrium and Kinetic Inhibition Assays Based upon Fluorescence Polarization, Methods in Enzymology, 74, 3-29 (1981).
Eremin et al., Intern. J. Environ. Anal. Chem. 71(2):137-146 (1998).

*Primary Examiner* — Lisa Cook
(74) *Attorney, Agent, or Firm* — Novak Druce +Quigg LLP

(57) ABSTRACT

A method of determining a concentration of analytes of interest in a sample reaction mixture is disclosed. The method can include measuring intensities of the polarized fluorescence of at least one comparative reaction mixture containing different, known amounts of the analytes of interest, and measuring the intensities of the polarized fluorescence of a sample reaction mixture. The method can also include determining the preliminary concentrations of the analytes of interest in the sample reaction mixture by comparing the measured intensities of the sample reaction mixtures at various time points. The margin of error for the preliminary concentration of the analytes of interest in the sample can be determined at the various time points. Finally, the concentration of the analytes of interest in the sample reaction mixture can be determined by comparing the preliminary concentrations and the respective margin of error at the given time points.

10 Claims, 8 Drawing Sheets

METHOD OF DETERMINING A CONCENTRATION OF ANALYTES OF INTEREST IN A SAMPLE

CROSS-REFERENCE TO RELATED APPLICATIONS

Figure 1A:
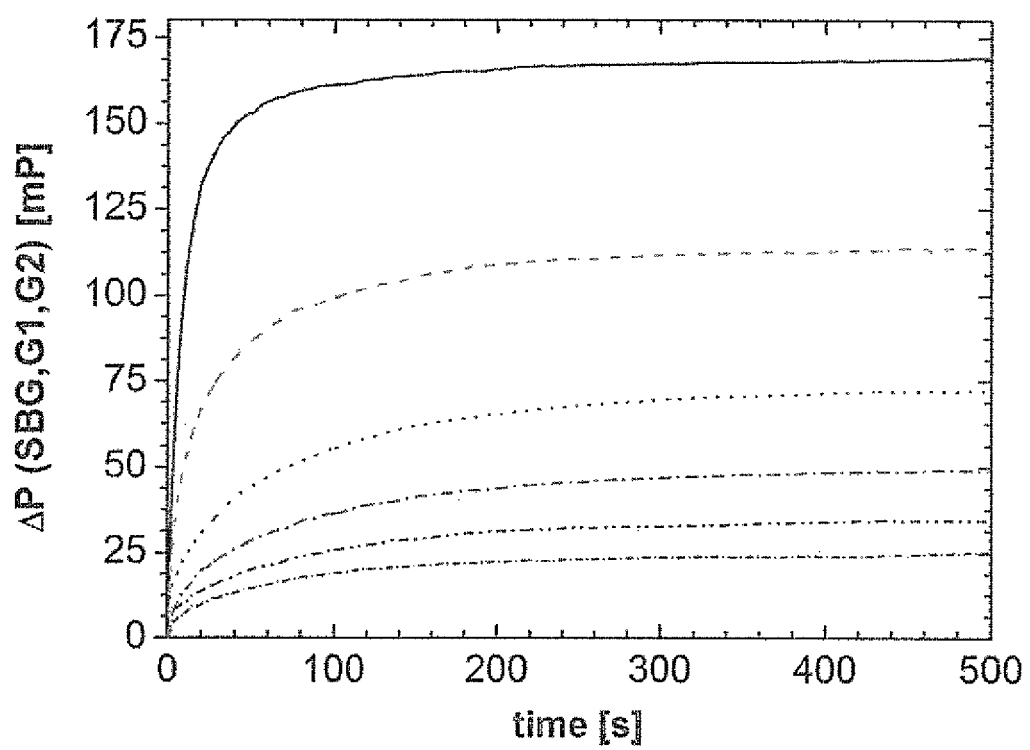

This application is a §371 national stage entry of International Application No. PCT/EP2008/059246, filed Jul. 15, 2008, which claims priority to European Patent Application No. 07114855.5, filed Aug. 23, 2007, and European Patent Application No. 07118281.0, filed Oct. 11, 2007, all of which are hereby incorporated by reference.

FIELD OF THE INVENTION

The present invention relates to a method of determining a concentration of analytes of interest in a sample reaction mixture (rapid kinetic assay).

BACKGROUND OF THE INVENTION

There is a high demand to determine the concentration of analytes of interest, which can be of environmental concern, such as fungal or microbial toxins (mycotoxins), which are fungal metabolites present in a large part of the world's food supply and pose a potential threat to food safety. In addition to this there is also a high demand to determine the concentration of analytes of interest in a sample of a mammal, such as drugs, steroids, hormones, proteins, peptides, lipids, sugars, receptors, nucleic acids, vitamins, etc, to identify an intoxication, control the medication of therapeutic drugs with a narrow therapeutic window, etc.

Assays, and in particular immunoassays, have been used in an effort to improve upon the success in detecting analyte substances at very low levels. For example, the use of such techniques has been prompted by the extraordinary successes that have been achieved in the measurement of biological substances by specific (immunological) binding moieties and techniques. Available evidence indicates that specific binding moieties, in particular antibodies, can be obtained even against low molecular weight organic compounds, such as pesticides or other haptens.

Any means of applying an (immuno-)chemical reaction to a detection problem ultimately relies upon a binding reaction occurring between analytes of interest and its specific binding moiety. One means by which this interaction can be employed in measurement and detection has come to be known as "competitive binding assay". In principle, this method requires two reagents in addition to the sample to be tested. These two reagents are a labeled form of the analyte to be detected or measured in a fixed concentration, and a binding moiety, preferably antibody or receptor, specifically directed against the analyte. The principle of this assay involves a preliminary measurement at one given time point of the binding of the labeled analyte (substance being detected) with its binding moiety and then, a determination at the given time point of the extent of the inhibition of this binding by known quantities of the unlabeled analytes of interest in the sample, which corresponds to the unknown concentration of the analytes of interest. From these data, a standard curve at the given time point can be constructed which shows the degree of binding of the labeled analyte under certain specified conditions as a function of concentration of the unlabeled analytes of interest added.

Another means by which this interaction can be employed in measurement and detection has come to be known as "non-competitive binding assay". In principle, this method requires only one reagent in addition to the sample to be tested. This reagent is a labeled form of the binding moiety, preferably antibody, receptor or enzyme, specifically directed against the analytes of interest. In principle this assay involves a direct measurement at one given time point of the binding of the labeled binding moiety with the analytes of interest in the sample followed by a determination at a given time point of the extent of intensity. From this data, a standard curve at the given time point can be constructed which shows the degree of binding by the labeled binding moiety with the analytes of interest under certain specified conditions as a function of concentration of the analytes of interest.

One way of implementing such (immuno-)assays is to employ a fluorescent label. Usually, fluorescent labeling of one of the reagents, e.g. the analyte used in known concentration, is important in carrying out the assay by means of fluorescence polarization and/or fluorescence intensity measurements. Unlike other assays, such as ELISA, no physical separation of bound form of the labeled analyte from free form is necessary. Therefore, a simple rapid optical measurement yields the essential information without physical separation of bound and free labeled materials.

Direct readout polarometer (having a machine time-constant of 0.1 seconds to several minutes) can be used to study slow kinetic reactions (reaction time-constant 10 seconds or longer) as well as reactions near or at equilibrium. These direct readout polarometer (defined as "static" polarometer) are capable of measuring both the degree of fluorescence polarization, $P=(V-H)/(V+H)$ and the sum of intensities of polarized fluorescence in horizontal and vertical direction (V+H). V–H (the absolute difference of the intensities of polarized fluorescence in horizontal and vertical direction) can also be measured and utilized as a parameter. Some binding moiety—analyte reactions can be slow enough such that they can be studied with the static polarometer. Other binding moiety-analyte reactions occur too rapidly (reaction milliseconds to seconds) to be monitored by the static fluorescence polarization or fluorescence intensity device. Fast reaction technology (e.g. stopped-flow methodology) has been combined with fluorescence polarization and fluorescence intensity techniques to study rapid binding moiety-analyte, preferably hapten-antibody, rapid antigen-antibody, rapid enzyme-substrate, rapid substrate-receptor reactions. Such rate assays should lead in principle to simplified and improved assays even when applied to the analysis of real analytes. Yet currently there are few fluorescence polarization or fluorescence intensity rate immunoassays as well as other rate assays involving substrates and receptors. This is because fluorescence polarization and fluorescence intensity stopped-flow devices are expensive, somewhat complicated, and at times limited by background problems. "Static" fluorescence polarometer rate immunoassays require large dilutions of fluorescent reactants and analytes to slow down these fast reactions so that a reasonable time frame (seconds to minutes) can be attained.

As mentioned already above, in conventional competitive or non-competitive fluorescence labeled homogenous assays the concentration of the analytes is determined at one predetermined time point of the reaction. Normally, the time point of establishing the concentration of the analytes of interest in the sample correlates to the equilibrium condition of the reaction or another predetermined time point $t=t_0+x$ (with $t_0$=the time point of addition of the last reaction component to the mixture and x=a time point of reaction) close to equilibrium condition. Thus, the time for measuring immuno-assays may take 5 minutes or more according to conventional procedures.

The sensitivity of assays, in the meaning of dependency of the concentration to the measured signal, has usually one optimal time period for a first concentration and a second optimal time period for a second concentration, where the margin of error is within a tolerable range. Due to the fact that only one measurement is taken at one time point, measuring errors and intolerable margin of error have a direct (intolerable) impact on the determined concentration of analytes in the sample.

In particular, when the determination of the concentration of analytes of interest is of environmental or health concern, there may be an interest that the tolerable margin of error is comparatively small and that the concentration is reliably determined.

Thus, there is a need to provide quick and reliable methods for determining the concentration of analytes of interests in a sample, wherein the margin of error is reliably within a tolerable limit. This will allow a person skilled in the art to provide a quick and reliable determination of concentration of analytes of interest, which may be in particular of environmental or health concern, so that reasonable precautions or counteractions may be undertaken.

SUMMARY OF THE INVENTION

At least part of the problems is solved by the present invention as claimed in the independent claims.

Accordingly, one aspect of the present invention relates to a method of determining a concentration of analytes of interest in a sample reaction mixture, which includes or is suspected to include the analytes of interest, comprising or consisting of the following steps:
  a) Measuring or providing intensities of the polarized fluorescence of one, two, three, four, five or more comparative reaction mixtures in vertical and horizontal direction over a given time period of the reaction, wherein each reaction mixture is separately present in a reaction vessel and respectively comprises
      (i) three components selected from the list consisting of a sample with a known concentration of analytes of interest, wherein the concentration differs for the respective comparative reaction mixtures, a fixed concentration of fluorescence labeled analyte and a fixed concentration of binding moieties directed to specifically bind to the analytes of interest and the fluorescence labeled analyte, wherein the time point ($t_{0_c}$) of addition of the third component in each comparative reaction mixture is respectively determined, or
      (ii) two components selected from the list consisting of a sample with a known concentration of analytes of interest, wherein the concentration differs for the respective comparative reaction mixtures, and a fixed concentration of fluorescence labeled binding moieties directed to specifically bind to the analytes of interest, wherein the time point ($t_{0_c}$) of addition of the second component in each comparative reaction mixture is determined respectively,
  b) Measuring intensities of the polarized fluorescence of a sample reaction mixture in vertical and horizontal direction over a given time period of the reaction, wherein the sample reaction mixture is present in a reaction vessel and comprises
      (i) three components selected from the list consisting of a sample which includes or is suspected to include analytes of interest, a fixed concentration of fluorescence labeled analyte and a fixed concentration of binding moieties directed to specifically bind to the analytes of interest and the fluorescence labeled analyte, wherein the time point ($t_{0_s}$) of addition of the third component is determined in the sample reaction mixture, or
      (ii) two components selected from the list consisting of a sample which includes or is suspected to include analytes of interest, and a fixed concentration of fluorescence labeled binding moieties directed to specifically bind to the analytes of interest, wherein the time point ($t_{0_s}$) of addition of the second component is determined in the sample reaction mixture,
  c) Determining preliminary concentrations of the analytes of interest in the sample reaction mixture by comparing the measured intensities of the sample reaction mixture at two, three, four, five or more time points of the reaction ($t_n = t_{0_s} + x_n$) with the intensities of the first, second, third, fourth, fifth and further comparative reaction mixture at the same time points of the reaction ($t_n = t_{0_c} + x_n$),
  d) Determining the margin of error for the preliminary concentration of the analytes of interest in the sample reaction mixture in step c) at the given time points ($t_n$), and
  e) Determining the concentration of the analytes of interest in the sample reaction mixture by comparing the preliminary concentrations and the respective margin of error at two, three, four, five or more given time points ($t_n$) and
      (i) Selecting a preliminary concentration at one given time point, where the margin of error is within a tolerable range, to be the concentration of the analytes of interest in the sample reaction mixture or
      (ii) Selecting two, three, four, five or more preliminary concentrations at two, three, four, five or more given time points, where the margin of error is respectively within a tolerable range, and determining the mean value thereof to be the concentration of the analytes of interest in the sample reaction mixture.

According to the present invention the term "comparative reaction mixtures" is defined as the reaction mixtures used for calibrations.

According to the present invention the term "sample reaction mixtures" is defined as the reaction mixtures used for the sample which includes or is suspected to include analytes of interest.

According to the present invention $t_{0_c}$ is defined as the starting time point of the reaction in a comparative reaction mixture, which correlates to the time point of addition of the last reagent in the assay. Accordingly, it is the time point of addition of the third reagent in a comparative assay and the second reagent in a non-competitive assay. The starting point $t_{0_c}$ is determined for the comparative reaction mixtures respectively.

According to the present invention $t_{0_s}$ is defined as the starting point of the reaction in the sample reaction mixture, which correlates to the time point of addition of the last reagent in the assay. Accordingly, it is the time point of addition of the third reagent in a comparative assay and the second reagent in a non-competitive assay.

According to the present invention $t_n = t_{0_s} + x_n$ is defined as n-number of time points during the reaction where, e.g., intensities are measured, wherein n is an integer of 2, 3, 4, 5 or more and x is the time period in seconds for the n-number of time points from the starting point of the reaction in the sample reaction mixture to the respective time points of measurement.

According to the present invention $t_n=t_{0_c}+x_n$ is defined as n-number of time points during the reaction where e.g. intensities are measured, wherein n is an integer of 2, 3, 4, 5 or more and x is the time period, preferably in seconds, for the n-number of time points from the starting point of the reaction in each of the comparative reaction mixtures to the respective time points of measurement.

The present invention is based on the finding that by evaluating the intensities of one, two, three, four, five or more comparative reaction mixtures with different known concentrations of analytes over a period of two, three, four, five or more time points of at least part, preferably a large part of the reaction and comparison with the intensities in the sample reaction mixture a more reliable concentration of analytes of interest in the sample reaction mixture may be determined, which is within a more tolerable margin of error.

A "calibration set" according to the present invention is a set of measurements of curves of, e.g., intensities over a given time period for the one, two, three, four, five or more comparative reaction mixtures with known concentration of analytes of interest. The measured intensities may be mathematically transformed ("graph"), e.g., $\Delta P$ over time ($\Delta Pt = P_t - P_{(t=0)}$), $\Delta r$ over time ($\Delta r = r_t - r_{(t=0)}$), $\Delta l$ over time ($\Delta l = l_t - l_{(t=0)}$), dP/dt over time, dr/dt over time, H over time, V over time etc.

According to FIGS. 1a), 1b), and 1c) a person skilled in the art denotes that the distance between the curves of different concentrations of zearalenone at $\Delta P$ over time (FIG. 1a), $\Delta r$ over time (FIG. 1b), or $\Delta l$ over time (FIG. 1c) is not the same over the entire time period. As the distances between the respective curves and the comparison with the intensities of the sample with unknown concentration relate to the accuracy of measurement, the evaluation over a substantial time period and not one time point of the reaction increases the sensitivity and also reduces the margin of error, when determining the concentration of the analytes of interest in the sample reaction mixture.

Further to this the calibration set enables a person skilled in the art to predetermine the time period wherein the margin of error of the concentration of analytes of interest is within a tolerable range. Accordingly, the optimal time period for measuring the sample can be predetermined. In particular, such time period for evaluation the intensities may be prior to the equilibrium condition, e.g. time period=$t_0$+30 sec to 240 sec, preferably time period=$t_0$+30 sec to 60 sec of the reaction with $t_0$ is the starting point of the reaction as defined before.

Accordingly, the present invention provides an advanced method for determining the concentration of analytes of interest in a sample, as:
- the optimal time period for determining the concentration in the sample may be prior to the equilibrium condition,
- the overall margin of error may be reduced by comparison of the data over the time period,
- real time results are provided and thus a quicker determination of the concentration than with conventional procedures is possible, and
- the determination of the concentration of analytes of interest in a sample may be conducted over a broader concentration range.

DETAILED DESCRIPTION

Preferred embodiments of the present invention are described in the following and in particular in the dependent claims and the figures.

The present invention relates to a method of determining a concentration of analytes of interest in a sample reaction mixture, which includes or is suspected to include the analytes of interest. "Analytes of interest" according to the present invention can be of environmental or health concern.

In one preferred embodiment, analytes of interest are fungal or microbial toxins (mycotoxins). In this case, the inventive method is preferably related to determining the concentration of mycotoxins selected from the group: aflatoxins, more preferably aflatoxins B1, B2, G1 and G2; ochratoxins, more preferably ochratoxin A (OTA), ochratoxin B, ochratoxin C, ochratoxin α and ochratoxin β, and most preferably ochratoxin A (OTA); type A-trichothecenes, more preferably T-2 toxin, HT-2 toxin, neosolaniol, monoacetoxy scirpenol and diacetoxyscirpenol; type B-trichothecenes, more preferably deoxynivalenol (DON), nivalenol, 3- and 15-acetoxynivalenol and fusarenon X; fumonisins, more preferably fumonisin B1 and fumonisin B2, and most preferably fumonisin B1; patulin; zearalenone; citrinin; cyclopiazonic acid; moniliformin; sterigmatocystin; alternaria toxins, more preferably tenuazonic acid, alternariol monomethyl ether, alternariol, altenuene and altertoxin I; ergot alkaloids, more preferably ergotamine, ergocornine, ergocristine, ergocryptine, agroclavine and ergometrine; *Aspergillus clavatus* toxins; *Aspergillus fumigatus* toxins; citreoviridin; *Fusarium* toxins; gliotoxin; griseofulvin; mycophenolic acid; b-nitropropionic acid; kojic acid; penicillic acid; *penicilium roqueforti*-toxin (PR-Toxin), more preferably roquefortines A, B and C; penitrem A; stachybotryotoxin toxins, more preferably satratoxins G and H; viomellein, vioxanthin, xanthomegnin; and walleminols.

More preferably the inventive method is being used for determining the concentration of mycotoxins selected from the group: deoxynivalenol, zearalenone, fumonisin, ochratoxin and aflatoxin.

In another embodiment of the present invention, the analytes of interest are selected from—but not limited to—the group consisting of pesticides, drugs, steroids, hormones, proteins, peptides, lipids, sugars, receptors, nucleic acids, vitamins, etc. For example, in one preferred embodiment, the analyte of interest is thyroxine, which is a major hormone secreted by the follicular cells of the thyroid gland.

The following Table 1 comprises a list of analytes of interest:

| CLASS | EXAMPLES |
| --- | --- |
| pesticides | acetochlor and other acetanilides, atrazin, simazine, triazine, 2,4-D, 2,4,5-T, dichlorprop, MCPA, MCPB, triclopyr, pentachlorophenol, DDT, isoproturon, methabenzthiazurone, metasulfuron-methyl, chlorsulfuron, propanil, paraquat, parathion-methyl, BTEX, nonylphenol, LAS |
| lipids | DHET |
| sugars | bacterial sugars, polysaccharides |
| peptides, proteins, receptors | IgG, albumin, receptors, KLH, LPH myoglobin, feto proteins, AT1 |
| oligonucleotides, DNA, RNA | of bacterial, animal, and/or plant origin, or specific sequences |
| toxins | zearalenone, deoxynivalenol, T-2, aflatoxins, ochratoxin, fumonisins, patulins, trichothecene, citrinin, cyclopiazonic acid, monoliformin, sterigmatocystin, alternaria-mycotoxins, ergot alkaloids |
| vitamins | vitamin B 12, vitamin C, folic acid |
| small molecules | chlorinated compounds, metals |
| therapeutic drugs, e.g., antiasmatics, antineoplastics, antiarythmics, | theophylline, doxorubicin, methotrexate, disopyramide, lidocaine, procainamide, propranolol, quinidine, N-acetyl-procainamide, Phenobarbital, phenotoin, pridon, valproic acid carbamazepine, ethosuximide, |

| CLASS | EXAMPLES |
|---|---|
| anticonvulsants, antibiotics, antiarthritics, antidepressants, etc. | cephalosporins, erythromycin, tetracyclin, vancomycin, gentamicin, amikacin, chloramphenicol, streptomycin, tobramycin, penicillin, salicylate, nortriptyline, amitriptoline, imipramine, desipramine, histamine, thyroxine, triiodothyronine, serotonin, etc. |
| drugs of abuse | morphine, heroin, hydromorphone, dihydrocodeine, pholcodine, amphetamine, etc. |
| steroids and hormones | esterone, estradiol, cortisol, testosterone, progesterone, chenodeoxycholic acid, digoxin, cholic acid, digitoxin, deoxycholic acid, lithocholic acid, etc. |
| prostaglandins | PGE, PGF, PGA, others |
| components of binding and reaction studies | antibodies, receptors, enzymes (i.e., proteases, nucleases, phosphatases) |

In one preferred embodiment, the binding moiety that specifically binds to the analytes of interest is selected of the group consisting of antibodies, receptors and enzymes. Preferably the binding moiety is an antibody. It is well known that a substance, when injected into an animal, stimulates the animal to produce an antibody. The antibody is capable of reacting with the injected substance in a highly specific manner. These antibodies belong to a group of serum proteins known as immunoglobulins. The production of these antibodies as a result of the injection of the antigen takes place over a period of many weeks, and depends upon the immunization schedule. In general, "good" antigens are usually of large molecular size (greater than 20,000 MW), partially digestible by enzymes and are recognized as being foreign by the antibody producing animal.

Many analytes of interest being of environmental or health concern do not have a large molecular weight, and would, therefore, appear to be incapable of stimulating antibody formation. However, this is not the case as so-called partial antigens or haptens can be produced and are capable of reacting with specific antibody. Haptens or partial antigens are defined as antigens which alone cannot induce antibody formation, but in conjugation with a suitable carrier can produce antibody against themselves, as well as against the carrier-hapten complex. Examples of carriers include ovalbumin, bovine serum albumin, fibrinogen, and many others. Conjugation may be carried out by methods known in the art (Coligan, J. E. et al. (Eds.) Current Protocols in Immunology, Chapter 9, Wiley Intersciences, New York, 1999).

The hapten, once conjugated with a suitable carrier, can stimulate antibody production. Some antibody will be produced which is highly specific in its reaction with the hapten alone. Therefore, by employing hapten-specific antibodies, the methods of the present invention can be used in the detection and quantitation of even low molecular weight organic compounds, such as pesticides.

Antibodies suitable for use in the methods of the present invention include polyclonal and monoclonal antibodies. Polyclonal antibodies can be prepared in accordance with known methods (Coligan, J. E, et al. (Eds.), Current Protocols in Immunology, Wiley Intersciences, New York, 1999). Monoclonal antibodies may be produced by methods known in the art. These methods include the immunological method described by Kohler and Milstein in Nature 256:495-497 (1975) and by Campbell in "Monoclonal Antibody Technology, The Production and Characterization of Rodent and Human Hybridomas" in Burdon et al. (Eds.), Laboratory Techniques in Biochemistry and Molecular Biology, Volume 13, Elsevier Science Publishers, Amsterdam (1985); and Coligan, J. E, et al. (Eds.), Current Protocols in Immunology, Wiley Intersciences, New York, (1999); as well as the recombinant DNA method described by Huse et al., Science 246: 1275-1281 (1989).

Antibodies against markers in normal human tissue and neoplasms are commercially available, for example, from Invitrogen Corporation (Carlsbad, Calif.), Advanced Immunochemical Inc. (Long Beach, Calif.) and RDI Division of Fitzgerald Industries, Intl. (formerly Research Diagnostics, Inc., Concord, Mass.). These include, but are not limited to, monoclonal and polyclonal antibodies against the following classes of analytes: proteins (e.g., enzymes, growth factors, cytokines), peptides, receptors (e.g., CD markers), toxins, infectious agents (e.g., viruses), steroids, hormones, lipids and lipoproteins). For example, antibodies against angiogenesis markers are commercially available, and such antibodies include those against the following receptors: CD31, CD34, Vascular Endothelial Growth Factor (VEGF), Vascular Endothelial Growth Factor C (VEGF-C) and Vascular Endothelial Growth Factor Receptor 3 (VEGFR-3). Also, antibodies against cancer markers are commercially available, such as those against the following: ALK, ALK 400, c-kit (CD117), COX-1, COX-2, EZH2, Ezrin, MAGE-A, Mesothelin, MTA1, NY-ESO-1, PDEF, PRAC, PSMA, RCAS1, thymidylate synthase and tyrosinase. Furthermore, antibodies against markers for specific types of cancer are commercially available. For example, commercially available antibodies against breast cancer markers include those against the following: BCA-225, Bcl-2, c-Met, Cathepsin D, CD63, cytokeratins, E-cadherin, EGFr, estrogen receptor, progesterone receptor, HER2, HER4, p53 and phospho-MAP kinase. Moreover, markers for colon cancer include, but are not limited to, CA 19-9, CEA, COX-1, Ezrin, MLH1, MSH2, MSH6, Platelet Derived Endothelial Cell Growth Factor (PD-ECGF), PRLr and Thymidylate Synthase (TS). Antibodies against these colon cancer markers, as well as markers for other specific cancers, diseases or disorders are also commercially available. Antibodies against apoptosis markers are also commercially available, and these markers include, for example, Bax, Bcl-2, Bcl-XL and PARP. Moreover, antibodies against cell cycle and cell proliferation markers are commercially available. Such cell cycle and cell proliferation markers include, but are not limited to, BrdU, Cyclin D1, Cyclin E, p21, Proliferating Cell Nuclear Antigen (PCNA) and S-Phase Kinase-Associated Protein 2 (SKP2). Antibodies against cellular proteins, such as, but not limited to, calcitonin, HLA DR, MGMT, nitrotyrosine and nNOS are also commercially available. Moreover, antibodies against cytoskeletal proteins, such as α-Tubulin, βTubulin, Actin, Desmin, GFAP, Myosin, Ubiquitin and Vimentin, are commercially available. Furthermore, antibodies against markers for lipoprotein metabolism are commercially available. Such antibodies include, for example, those against HDL, LDL, APOE, ApoE2, LDL receptors, etc. The abbreviations used herein for the markers are well known in the art.

Furthermore, antibodies against pesticides and herbicides are commercially available from such companies as Guildhay, Ltd. (Guildford, Surrey, England). For example, antibodies against 2,4-D, aldrin, atrazine, chlortoluron, diuron, isoproturon, MCPA, mecoprop, paraquat, simazine, solanine, etc. are commercially available.

The present invention is not, in any way, limited to the specific examples provided herein of analytes of interest and antibodies that specifically bind to the analytes.

In other preferred embodiments of the present invention, the binding moiety that specifically binds to the analytes of interest are receptors. For example, if a hormone carrying a fluorescent label attaches to its receptor, the hormone is thereby largely immobilized and this immobilization is registered by an increase in the polarization of the emission from the attached fluorescent label. In addition to antigen-antibody, hapten-antibody and hormone-receptor interactions, the methods of the present invention can also be applied to enzyme-substrate, protein-DNA, peptide-antibody and ligand-receptor interactions.

In one embodiment of the present invention, the binding moiety that specifically binds to the analytes of interest and its fluorescent reactant is attached to a solid substrate. For example, a specific binding moiety, such as an antibody, can be deposited on a glass, plastic or paper substrate. Substrates can include various microporous filters, such as PVDF filters, nitrocellulose filters, cellulosic filters and the like. In one example, the antibody can first be bound to a substrate, such as PVDF. Second, the antibody on the substrate can be exposed to a fluorescent-labeled form of an analyte of interest. Then, a study of the inhibition of the binding of this fluorescent conjugate by a sample thought to contain the analyte of interest is performed. In particular, one can observe a change in P, V–H and/or V+H which occurs in the presence of the sample. The competitive-inhibition assay of the present invention can be applied to the simultaneous analysis of multiple analytes of interest in a sample using analytes labeled with different fluorescent wavelength conjugates. This would reduce the time and effort involved in multianalyte, multi-sample analyses.

The analysis of the determination of the concentration of the analytes of interest may be performed, for example, in water, serum, blood, urine or other bodily fluids. Moreover, the analysis may be performed in milk, wine, juices and food extracts. If necessary, suitable conventional buffer solutions may be added, preferably phosphate buffered saline (PBS).

The method according to the invention is directed to measure the intensities of polarized fluorescence of one, two, three, four, five or more reaction mixtures with differing concentrations of analytes of interests over a time period to receive a calibration set with which the intensities measured over a time period for one or more sample mixtures are compared with. The order of conducting the measurements is not strict, i.e. the measurements of the calibration set or the measurement of the sample mixture can either be conducted first. The measurement will be conducted, however, for (i) a competitive reaction or (ii) a non-competitive reaction.

In case a competitive reaction is monitored over a time period, the comparative reaction mixture comprises or consists of at least three components selected of a sample with a known concentration of analytes of interest, a fixed concentration of fluorescence labeled analytes of interest and a fixed concentration of binding moieties directed to specifically bind to the analytes of interest. This means that the binding moiety binds to the fluorescence labeled and the unlabeled analytes of interest and the measured intensity will relate to the amount of binding moiety-fluorescence labeled analyte-complexes. Accordingly, the concentration of the unlabeled analytes of interest can be determined.

In case a non-competitive reaction is monitored over a time period, the comparative reaction mixture comprises or consists of at least two components selected from the list consisting of a sample with a known concentration of analytes of interest, and a fixed concentration of fluorescence labeled binding moieties directed to specifically bind to the analytes of interest. This means that the fluorescence labeled binding moieties bind to the analytes of interest directly and thus the measured intensity correlates to the concentration of the analytes of interest directly.

Preferably, the fluorescent labels chosen to form the conjugate with the analyte or the binding moieties are selected from any number of fluorescent moieties. The choice of fluorescent moiety is to a large extent a matter of convenience once a coupling chemistry has been selected. Virtually any fluorophore having a fluorescence lifetime of between 0.1 and 50 nanoseconds and having an excitation wavelength of 350 to 800 nanometers is suitable for purposes of the present invention. For a detailed listing of fluorophores, which are commercially available, see Handbook of Fluorescent Probes and Research Chemicals, ed. Karen Larison, by Richard P. Haugland, Ph.D., 5th ed., 1992, published by Molecular Probes, Inc. Some examples of suitable fluorescent moieties include the following: 7-AAD, Acridine Orange, Alexa 488, Alexa 532, Alexa 546, Alexa 568, Alexa 594, Aminonapthalene, Benzoxadiazole, BODIPY 493/504, BODIPY 505/515, BODIPY 576/589, BODIPY FL, BODIPY TMR, BODIPY TR, Carboxytetramethylrhodamine, Cascade Blue, Coumarin, CY2, CY3, CY5, CY9, Dansyl Chloride, DAPI, Eosin, Erythrosin, Ethidium Homodimer II, Ethidium Bromide, Fluorescamine, Fluorescein, FTC, GFP (e.g. yellow shifted mutants T203Y, T203F, S65G/S72A), Hoechst 33242, Hoechst 33258, IAEDANS, Indopyras Dye, Lanthanide Chelate, Lanthanide Cryptate, Lissamine Rhodamie, Lucifer Yellow, MANT, MQAE, NBD, Oregon Green 488, Oregon Green 514, Oregon Green 500, Phycoerythrin, Porphyrin, Propidium Iodide, Pyrene, Pyrene Butyrate, Pyrene Maleimide, Pyridyloxazole, Rhodamine 123, Rhodamine 6G, Rhodamine Green, SPQ, Texas Red, TMRM, TOTO-1, TRITC, YOYO-1, Vitamin B12, flavin-adenine dinucleotide, 6-carboxy-X-rhodamine, nicotinamideadenine, and dinucleotide. Preferably, the fluorescent conjugate would have a fluorescent wavelength different from competing fluorescent substances which may occur in host samples of interest, e.g., blood serum, urine, tissue and extracts thereof.

For measuring the comparative or sample reaction mixtures, conventional polarometer may be used. Polarometer denotes an instrument for measuring the degree of polarization as contrasted to optical rotation. The solution to be measured is first excited in a standard cell by linearly polarized light of appropriate wavelength. The emission fluorescent beam (with appropriate filters) then passes through a rapidly rotating polarizer and onto a photomultiplier tube whose output is fed into a computer which calculates e.g. the fluorescence polarization, $P=(V-H)/(V+H)$, Polarized Fluorescence Intensity ($I=V+H$), absolute Difference of the polarized Fluorescence Intensity (V–H), and the total fluorescence intensity ($I_f=V+2H$), as well as the following mathematical derivatives such as $d(V+H)/dt$, $d(V-H)/dt$, $dP/dt$, $dr/dt$. V and H denote intensities of vertically polarized and horizontally polarized components in fluorescent light. Alternatively, a "T-format" polarometer using two photomultiplier tubes set at right angles to the excitation source and each having polarizing filters place in a mutually orthogonal position. Provision is made for automatic deduction of the blank. Temperature control of the cell compartment is maintained with an appropriate thermostat.

Direct readout polarometer are commercially available. For example, such instruments are available from the following vendors: BMG Labtech GmbH, Offenburg, Germany; JASCO Corporation, Tokyo, Japan; Tecan Schweiz AG, Hännedorf, Switzerland; Bioscan, Inc, Washington, D.C.; Molecular Devices Corporation, Sunnyvale, Calif.; Perkin Elmer Life and Analytical Sciences, Inc., Wellesley, Mass.; Photon Technology International, Inc., Birmingham, N.J.; Abbott GmbH & Co. KG, Wiesbaden, Germany; Diachemix Corp. (USA), Whitefishbay, Wis.; and Invitrogen Corp., Carlsbad, Calif. As described above, the inherent sensitivity of fluorescence measurements can be used in monitoring the extent of reaction as a fluorescent reactant, F, combines with its macromolecular partner, R:

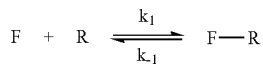

where $k_1$ is the forward reaction and $k_{-1}$ is the back reaction such that $(k_1)(k_{-1})=K_{(eq)}$.

The ratio of bound to free fluorescent material in the equation above can be directly related to fluorescence polarization and intensity parameters, as set out e.g. in Dandliker, et al, (1969) Immunochemistry, 6, 125.

As the measurement of the intensities are carried out over a time period when the reaction occurs, it is essential to determine when the reaction starts so that a meaningful comparison of different measurements of different reactions can be conducted. This starting time point ($t_{0_c}$) used for the first, second, third, fourth, fifth and further comparative reaction mixture with differing concentrations of the analytes of interest and the starting time point ($t_{0_s}$) used for the sample reaction mixture is the time point where (i) in the competitive assay the third component or (ii) in the direct assay the second component is added. Usually the order of addition of the reaction components is not strict.

In a preferred embodiment, the sample with the known concentration of the analytes of interest of the comparative reaction mixtures or the sample including or suspected to include the analytes of interest of the sample reaction mixture is added first to the reaction vessel (preferably cuvette, microtiter plate, etc.). Accordingly, the background fluorescence intensity can be measured and, if necessary, be incorporated into the calculation of the concentration.

In a competitive reaction the second component can be the binding moiety or the fluorescence labeled analytes of interest. The respective background intensities are preferably measured and, if necessary, incorporated when determining the concentration of analytes of interest in the sample reaction mixture.

In case the measurement of the intensities of the reaction mixtures for the calibration set is carried out on different polarometer, preferably a device-specific G-factor for the polarometer is used so that the comparison of the measurements in particular on different polarometer is less erroneous.

In particular, in case measurements of intensities of different comparative reaction mixtures with known different concentrations of analytes of interests are provided (calibration set), then the G-factor of the polarometer used are also taken into account for the determination of the concentration of analytes of interest.

Preferably, the time period for measuring the intensities of the comparative reaction mixtures comprising differing concentrations of the analytes of interest is from the starting point of the reaction ($t_{0_c}$) until equilibrium (full reaction).

The sample reaction mixture can also be measured from the start of the reaction ($t_{0_s}$) until the equilibrium. Preferably, the time period may be predetermined over a portion of the full reaction in dependency of a tolerable margin of error determined with respect to the resulting calibration curve as set out in the following. Even more preferably the time period is close to ($t_{0_s}$) so that a quick result can be derived.

As an example, in case the equilibrium condition starts after 5 minutes, the predetermined time points for measuring the sample reaction mixture may be $t_n=t_{0_s}+x_n$ with n-number of time points and n is an integer of 2, 3, 4, 5 or more and x is a time period of 15 sec to 120 sec, more preferably x is a time period of 20 sec to 100 sec. These time points are predetermined on basis of the calibration sets and the expected margin of error. The mean value of the determined preliminary concentrations of the analytes of interest within this predetermined time period are evaluated to be the concentration of the analytes of interest in the sample.

After measuring the intensities of the comparative reaction mixtures with different concentrations and the sample reaction mixture with unknown concentration of the analytes or using a provided calibration set of the comparative reaction mixtures, preliminary concentrations of the analytes of interest in the sample are determined by comparing the measured intensity of the sample reaction mixture at two, three, four, five or more time points (n) of the reaction ($t_n=t_{0_s}+x_n$) with the intensities of the first, second, third, fourth, fifth and further comparative reaction mixture at the same time points of the reaction ($t_n=t_{0_c}+x_n$). This means that by using the measured data or a mathematical transformations thereof the correlating preliminary concentration is determined.

In a further step, the margin of error for the preliminary concentration of the analytes of interest in the sample is determined at the given time points ($t_n$). Usually, this can be conducted by transforming the calibration set, where the measured data is taken over time, into a calibration curve at one time point, where the measured data is taken over the concentration of the reaction mixtures and the discrete data points are interpolated. Thus, in the meaning of the present invention, the term "calibration curve" relates to an interpolated function which is fitted to the discrete measured data points over the concentration of the comparative reaction mixtures at one time point. The margin of error, for each time point, is then usually determined by using the slope of the calibration curve in the point/range of the predetermined concentration and optionally the measuring error.

Finally, the concentration of the analytes of interest in the sample reaction mixture is determined by comparing the preliminary concentrations and the respective margin of error and
(i) Selecting a preliminary concentration at one given time point, where the margin of error is within a tolerable range, to be the concentration of the analytes of interest in the sample reaction mixture or
(ii) Selecting two, three, four, five or more preliminary concentrations at two, three, four, five or more given time points ($t_n$), where the margin of error is respectively within a tolerable range, and determining the mean value thereof to be the concentration of the analytes of interest in the sample reaction mixture.

The tolerable range of margin of error varies and can be dependent on the specific analytes of interest or specific areas of concern. Thus, the person skilled in the art will decide which range of margin of error is tolerable and applicable.

Preferably, the mean value of concentration is determined for the concentration of the analytes of interest, as by averaging the concentrations the margin of error may again be lowered. As the intensities are measured over a time period of the reaction, the specific time periods where the margin of error is within a tolerable range can ideally be determined.

FIGURES

Figure 1B:
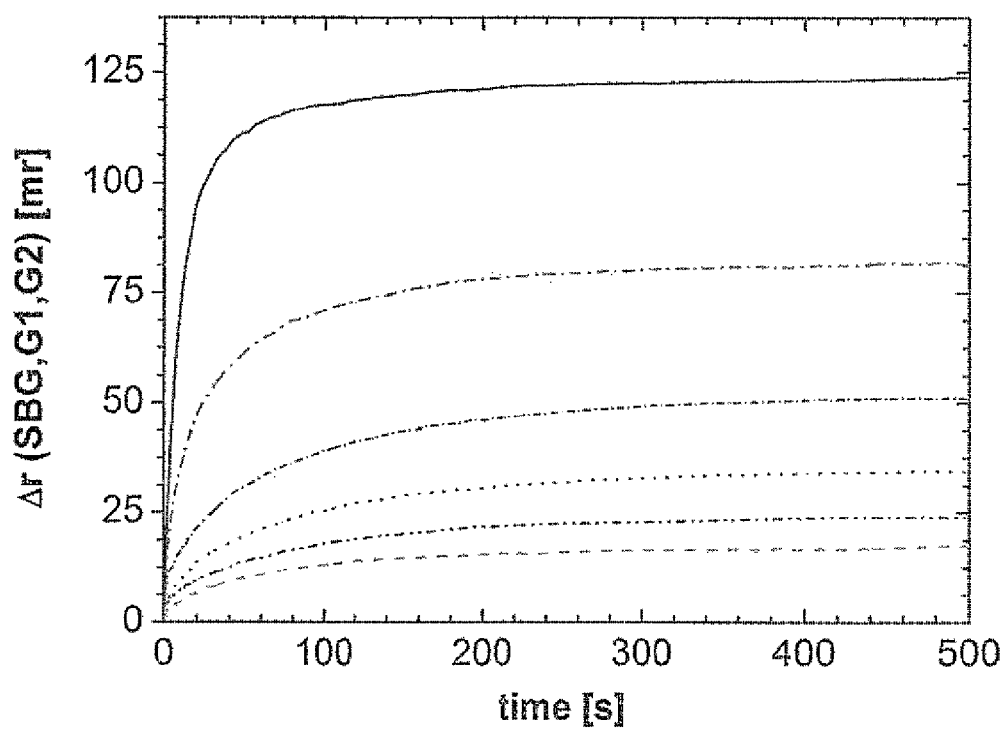
Figure 1C:
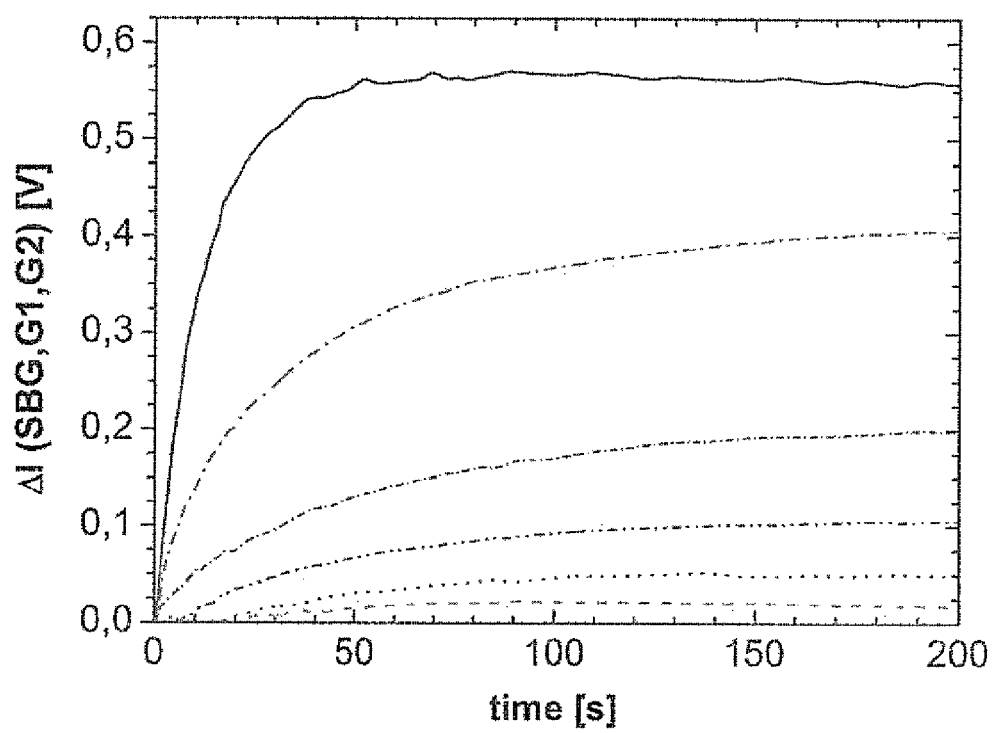

FIG. 1a) shows a graph of ΔP [mP] over time [s] as the calibration set of different concentrations of zearalenone in PBS (phosphate buffered saline), FIG. 1b) shows a graph of Δr [mr] over time [s] as the calibration set of different concentrations of zearalenone in PBS, and FIG. 1c) shows a graph of Δl [V] over time [s] as the calibration set of different concentrations of zearalenone in PBS.

Figure 2A:
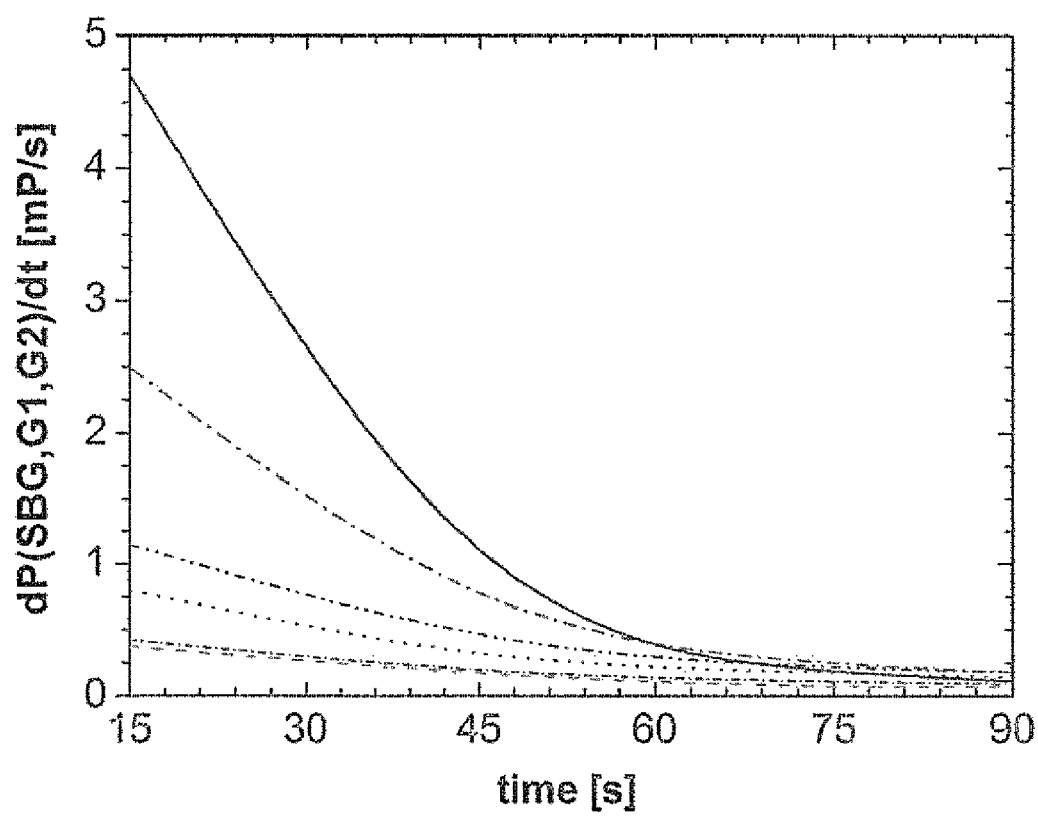

FIG. 2a) shows a graph of dP/dt [mP/s] over time [s], with t<30 seconds, as the calibration set of different concentrations of zearalenone in PBS.

Figure 2B:
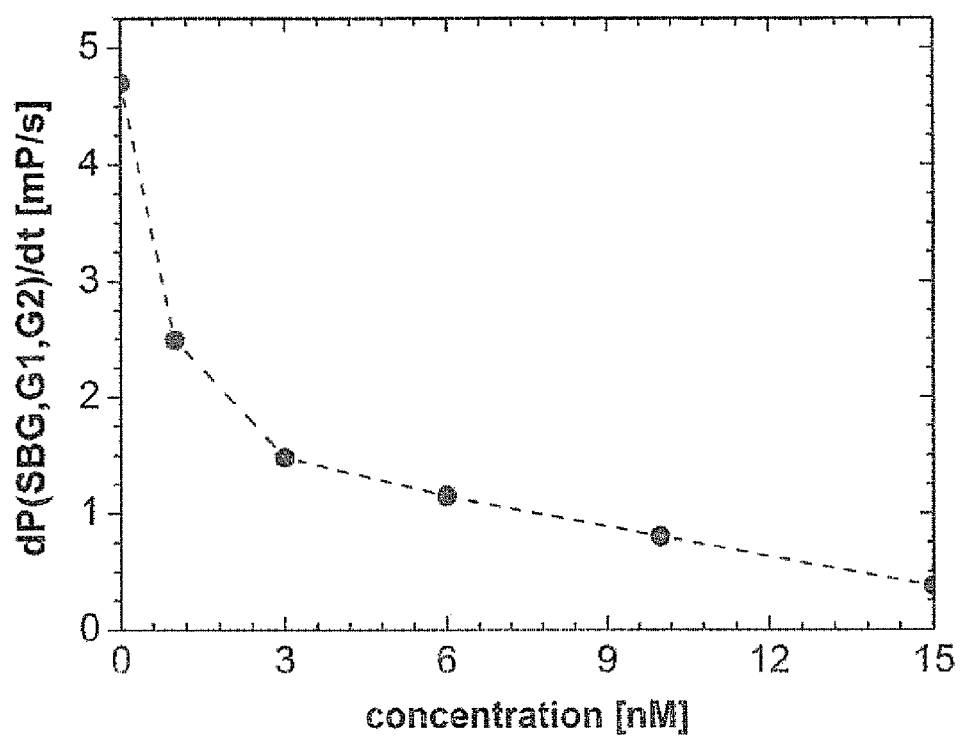

FIG. 2b) shows a graph of dP/dt [mP/s] over concentration [nM] as the calibration curve of different concentrations of zearalenone in PBS at one specific time point.

Figure 2C:
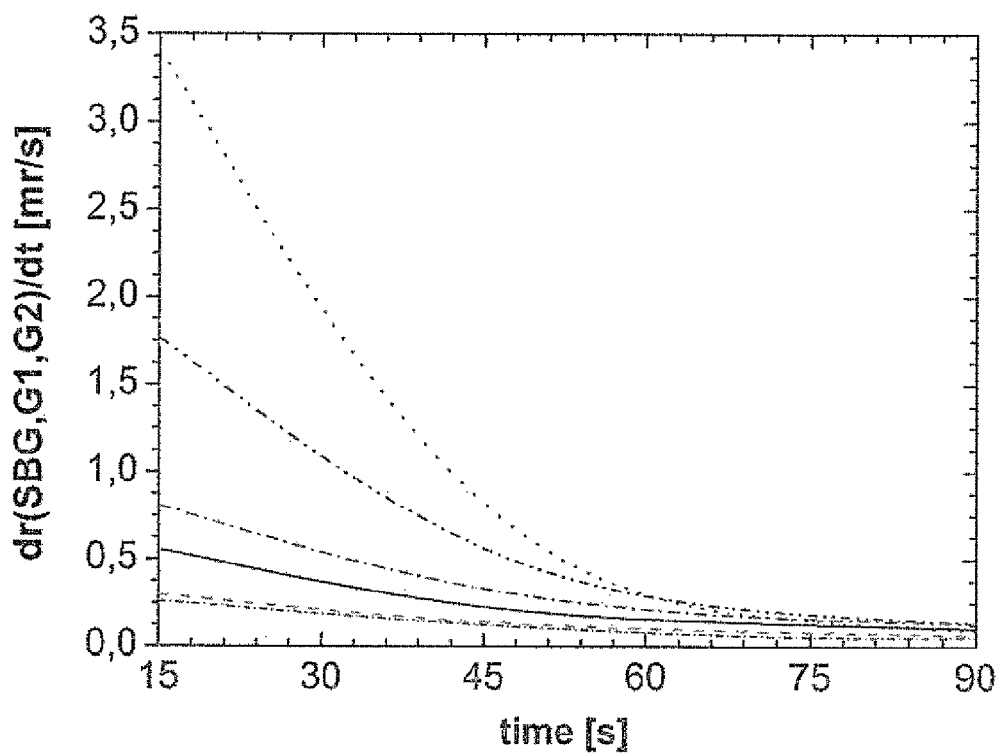

FIG. 2c) shows a graph of dr/dt [mr/s] over time [s], with t<30 seconds, as the calibration set of different concentrations of zearalenone in PBS.

Figure 2D:
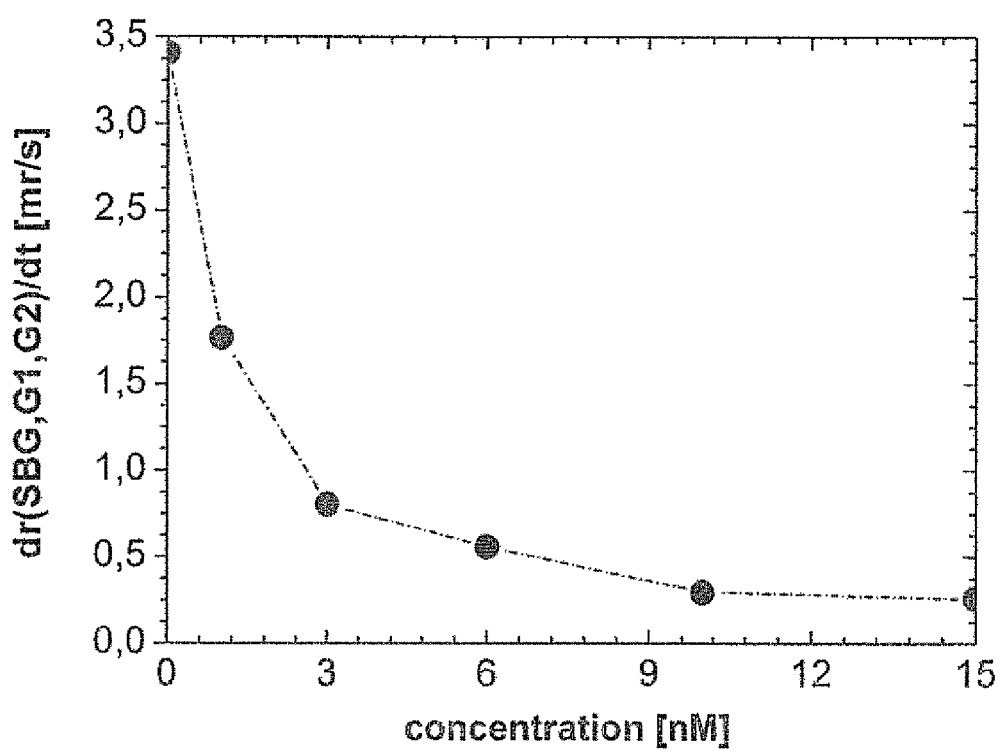

FIG. 2d) shows a graph of dr/dt [mr/s] over concentration [nM] of as the calibration curve of different concentrations of zearalenone in PBS at one specific time point.

Figure 3:
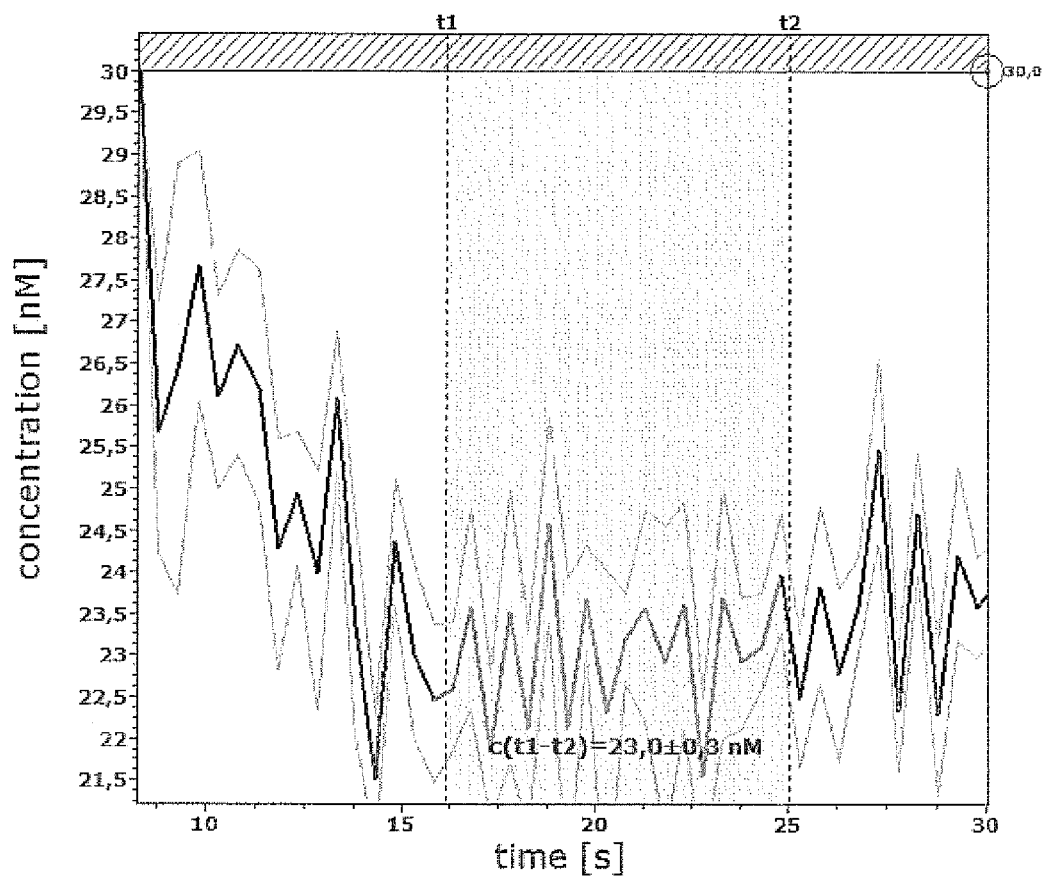

FIG. 3) shows a graph of the determined concentration [nM] of analytes of interest over time [s] by using a ΔP calibration set.

DETAILED DESCRIPTION OF THE FIGURES

Experimental set up for the respective calibration sets or calibration curves in the figures:
a) cuvette 2.5 ml PBS buffer pH 7.4, 10% MeOH
b) Concentrations of zearalenone respectively used: 0 nM, 3 nM, 6 nM, 10 nM, 15 nM
c) Concentration of Fluorescence Label respectively used: 1 nM fluorescently labeled zearalenone
d) Start of the binding reaction: addition of 20 μl of an 1:10 diluted solution of a polyclonal Antibody (rabbit) specific against zearalenone at t=0 sec.

In FIG. 1a) ΔP refers to the change of fluorescence polarization P=(V−H)/(V+H) measured [mP] as the calibration set of the different concentrations of zearalenone in PBS over time [s].

In FIG. 1b) Δr refers to the change of fluorescence anisotropy r=(V−H)/(V+2H) measured in [mr] as the calibration set of the different concentrations of zearalenone in PBS over time [s].

In FIG. 1c) Δl refers to the change of overall fluorescence intensity I=V+2H measured in [V] as the calibration set of different concentrations of zearalenone in PBS over time [s].

In FIG. 2a) the derivative of dP/dt over time is shown as a calibration set of different concentrations of zearalenone in PBS over time [s].

In FIG. 2b) the derivative of dP/dt over concentration is shown as a calibration curve of different concentrations [nM] of zearalenone in PBS at one specific time point.

In FIG. 2c) the derivative of dr/dt over time is shown as a calibration set of different concentrations of zearalenone in PBS over time [s].

In FIG. 2d) the derivative of dr/dt over concentration is shown as a calibration curve of different concentrations [nM] of zearalenone in PBS at one specific time point.

The person skilled in the art denotes from these graphs that the distance between the curves of the calibration set differs over time. Further to this the person skilled in the art takes from FIG. 1a) and FIG. 1b) that the proportions in the reaction change with respect to ΔP or Δr. From FIG. 1c) the person skilled in the art takes that the quantity yield in the reaction changes with respect to Δl. Thus, the sensitivity by using a method according to the invention is higher in contrast to a one time point measurement in the state of the art, as the margin of error is reduced by using different time point of comparing the measurements.

In FIG. 3 the determined preliminary concentrations of analytes of interest in a sample reaction mixture are shown over 0 sec to 30 sec of the reaction using a ΔP calibration set. A skilled person takes from the margin of error, that in the first 10 sec of the reaction the margin of error is higher than in the further reaction time. In the present case of FIG. 3 the $t_n = t_{0_s} + x_n$ is used where n is the number of 2, 3, 4, 5 or more time points and x is a time period of 16 sec to 25 sec, which has been chosen for evaluating the mean value of the predetermined concentration to be the concentration of the analytes of interest in the sample reaction mixture.

EXAMPLES

Example 1

Set Up of the Inventive Method Using a Competitive Reaction

1) Addition of the sample with unknown or known concentration of analytes,
2) Measurement of the background intensities,
3) Addition of the fluorescence labeled analytes of interest,
4) Determination of the device specific G-factor for the polarometer used by determination of the HH and HV signals using excitation of the mixture in horizontal direction and subsequent correction of the VH and VV intensities on the basis of G,
5) Addition of the binding moiety, preferably an antibody or receptor specifically binding to the analytes of interest and the fluorescence labeled analytes of interest,
6) Determining of H and V signals over time of the respective reaction mixtures or sample mixture, and
7) Determination of the concentration of the analytes in the sample by comparison of the intensities over a time period and incorporating the relevant margin of error and measuring error.

The set up is first conducted with comparative reaction mixtures of different known concentrations to represent a calibration set. These data will be stored in appropriate devices.

Subsequently the sample reaction mixture including or suspected to include the analytes of interest is measured according to the set up as described above.

The difference of the inventive method over the methods presented by the state of the art is that in addition to the measured intensity parameter correlating to a specific concentration, the time period is a further factor which reduces the margin of error of the determination of concentration in the sample.

The invention claimed is:
1. Method of determining a concentration of analytes of interest in a sample reaction mixture, which includes or is suspected to include the analytes of interest, comprising the following steps
  a) measuring or providing intensities of the polarized fluorescence of one, two, three, four, five or more comparative reaction mixtures in vertical and horizontal direction over a given time period of the reaction, wherein each comparative reaction mixture is separately present in a reaction vessel and respectively comprises
    i. three components selected from the list consisting of a sample with a known concentration of analytes of interest, wherein the concentration differs for the respective comparative reaction mixtures, a fixed concentration of fluorescence labeled analyte and a fixed concentration of binding moieties directed to specifically bind to the analytes of interest and the fluorescence labeled analyte, wherein the time point ($t_{0c}$) of addition of the third component in each comparative reaction mixture is respectively determined, or ii. two components selected from the list consisting of a sample with a known concentration of analytes of interest, wherein the concentration differs for the respective comparative reaction mixtures, and a fixed concentration of fluorescence labeled binding moieties directed to specifically bind to the analytes of interest, wherein the time point ($t_{0c}$) of addition of the second component in each comparative reaction mixture is determined respectively, b) measuring intensities of the polarized fluorescence of a sample reaction mixture in vertical and horizontal direction over a given time period of the reaction, wherein the sample reaction mixture is present in a reaction vessel and comprises i. three components selected from the list consisting of a sample which includes or is suspected to include analytes of interest, a fixed concentration of fluorescence labeled analyte a fixed concentration of binding moieties directed to specifically bind to the analytes of interest and the fluorescence labeled analyte, wherein the time point ($t_{0s}$) of addition of the third component is determined in the sample reaction mixture, or ii. two components selected from the list consisting of a sample which includes or is suspected to include analytes of interest, and a fixed concentration of fluorescence labeled binding moieties directed to specifically bind to the analytes of interest, wherein the time point ($t_{0s}$) of addition of the second component is determined in the sample reaction mixture, c) determining the preliminary concentrations of the analytes of interest in the sample reaction mixture by comparing the measured intensities of the sample reaction mixture at two, three, four, five, or more time points of the reaction ($t_n=t_{0s}+x_n$) with the intensities of the first, second, third, fourth, fifth and further comparative reaction mixture at the same time points of the reaction ($t_n=t_{0c}+x_n$), d) determining the margin of error for the preliminary concentration of the analytes of interest in the sample in step c) at the given time points ($t_n$), and e) determining the concentration of the analytes of interest in the sample reaction mixture by comparing the preliminary concentrations and the respective margin of error at two, three, four, five or more given time points ($t_n$) and i. selecting a preliminary concentration at one given time point, where the margin of error is within a tolerable range, to be the concentration of the analytes of interest in the sample or ii. selecting two, three, four, five or more preliminary concentrations at two, three, four, five or more given time points, where the margin of error is respectively within a tolerable range, and determining the mean value thereof to be the concentration of the analytes of interest in the sample.

2. Method according to claim 1, wherein the background intensities of the components of the comparative reaction mixtures, the sample reaction mixtures, or both are measured.

3. Method according to claim 1, wherein the intensities of the comparative reaction mixtures in step a) are provided.

4. Method according to claim 1, wherein the device specific G-factor is determined for one or more polarometer used to measure the intensities in step a) and/or step b).

5. Method according to claim 1, wherein the margin of error of the preliminary concentration of the analytes of the sample at specific time points is determined by the slope of the preliminary concentration in the calibration curve of the measured intensities of the reaction mixtures over the respective concentration for the respective time points ($t_n$) and optionally the measuring error.

6. Method according to claim 1, wherein the measurements of the intensities are carried out by polarometer of the T-format or the L-format.

7. Method according to claim 1, wherein the analytes of interests are selected of the group consisting of mycotoxins, pesticides, drugs, steroids, hormones, proteins, peptides, lipids, sugars, receptors, nucleic acids, and vitamins or combinations thereof.

8. Method according to claim 1, wherein the binding moieties directed to specifically bind to the analytes of interest are selected from the group consisting of antibodies, receptors and enzymes.

9. Method according to claim 1, wherein the step e) the determination of the concentration of analytes of interests is carried out by selecting time points prior to equilibrium.

10. Method according to claim 9, wherein the time points are close to ($t_{0s}$).

\* \* \* \* \*